United States Patent
Taniguchi et al.

(10) Patent No.: US 10,533,151 B2
(45) Date of Patent: Jan. 14, 2020

(54) METHOD FOR PRODUCING CELL CONCENTRATE, AND CELL SUSPENSION TREATMENT SYSTEM

(71) Applicant: KANEKA CORPORATION, Osaka-shi, Osaka (JP)

(72) Inventors: Shuhei Taniguchi, Settsu (JP); Nobuyoshi Umeda, Settsu (JP); Takaaki Sakashita, Kanazawa (JP); Hiroshi Sakurai, Kanazawa (JP)

(73) Assignee: KANEKA CORPORATION, Osaka-Shi, Osaka (JP)

( * ) Notice: Subject to any disclaimer, the term of this patent is extended or adjusted under 35 U.S.C. 154(b) by 0 days.

(21) Appl. No.: 16/142,857

(22) Filed: Sep. 26, 2018

(65) Prior Publication Data

US 2019/0024037 A1 Jan. 24, 2019

Related U.S. Application Data (62) Division of application No. 14/906,320, filed as application No. PCT/JP2014/068936 on Jul. 16, 2014, now Pat. No. 10,113,144.

(30) Foreign Application Priority Data

Jul. 23, 2013 (JP) ................. 2013-152755

(51) Int. Cl.
 *C12M 1/34* (2006.01)
 *A61M 1/02* (2006.01)
 (Continued)

(52) U.S. Cl.
 CPC .......... *C12M 41/46* (2013.01); *A61M 1/0218* (2014.02); *A61M 1/0281* (2013.01);
 (Continued)

(58) Field of Classification Search
 CPC ...... C12M 41/46; C12M 41/44; C12M 33/04; C12M 27/00; C12M 41/48; C12M 47/02;
 (Continued)

(56) References Cited

U.S. PATENT DOCUMENTS

| 4,964,976 A | 10/1990 | Lysaght et al. |
| 5,055,198 A | 10/1991 | Shettigar |

(Continued)

FOREIGN PATENT DOCUMENTS

| JP | 3012689 B2 | 2/2000 |
| JP | 2007-524396 A | 8/2007 |

(Continued)

OTHER PUBLICATIONS

International Search Report, issued in PCT/JP2014/068936, dated Aug. 12, 2014.
(Continued)

*Primary Examiner* — Sean C. Barron
(74) *Attorney, Agent, or Firm* — Birch, Stewart, Kolasch & Birch, LLP (57) ABSTRACT

In a method for producing a cell concentrate using a cell suspension treatment system including a storage container of a cell suspension, which has a solution inlet port, a circulation outlet port, and a circulation inlet port, a cell suspension treatment device for concentrating the cell suspension by separating liquid from the cell suspension by filtration, the device including a container having a cell suspension introduction port, a cell suspension lead-out port, and a filtrate outlet, which is filled with a hollow fiber separation membrane, a circulation circuit for concentrating the cell suspension while circulating the cell suspension between the storage container and the cell suspension treatment device, a collection container of a cell concentrate obtained by concentration, a collection path for feeding the cell concen-
(Continued)

trate to the collection container, an injection path for injecting a solution into the solution inlet port of the storage container, and a detecting unit.

7 Claims, 4 Drawing Sheets

(51) Int. Cl.
  *A61M 1/34* (2006.01)
  *A61M 1/36* (2006.01)
  *C12M 1/00* (2006.01)
  *C12M 1/02* (2006.01)
  *C12M 1/26* (2006.01)
  *C12M 1/36* (2006.01)
(52) U.S. Cl.
  CPC ............ *A61M 1/34* (2013.01); *A61M 1/3403* (2014.02); *A61M 1/3406* (2014.02); *A61M 1/3496* (2013.01); *A61M 1/3603* (2014.02); *A61M 1/3621* (2013.01); *A61M 1/3643* (2013.01); *A61M 1/3644* (2014.02); *A61M 1/3692* (2014.02); *C12M 27/00* (2013.01); *C12M 33/04* (2013.01); *C12M 41/44* (2013.01); *C12M 41/48* (2013.01); *C12M 47/02* (2013.01); *A61M 1/3626* (2013.01); *A61M 2205/3389* (2013.01); *A61M 2205/3393* (2013.01)
(58) Field of Classification Search
  CPC .............. A61M 1/3403; A61M 1/3406; A61M 1/3643; A61M 1/3621; A61M 1/3496; A61M 1/34; A61M 1/0281; A61M 1/3692; A61M 1/3644; A61M 1/3603; A61M 2205/3393; A61M 1/3626; A61M 2205/338; A61M 1/0218
  See application file for complete search history.

(56) References Cited

U.S. PATENT DOCUMENTS

| | | | | |
|---|---|---|---|---|
| 6,302,860 | B1* | 10/2001 | Gremel | A61M 1/3627 210/436 |
| 7,201,870 | B2* | 4/2007 | Olsen | A61M 1/3627 210/645 |
| 7,204,958 | B2* | 4/2007 | Olsen | A61M 1/32 210/645 |
| 7,335,334 | B2* | 2/2008 | Olsen | A61M 1/32 210/645 |
| 7,704,455 | B2* | 4/2010 | Olsen | A61M 1/3627 210/645 |
| 7,740,800 | B2* | 6/2010 | Olsen | A61M 1/3627 210/645 |
| 2001/0035377 | A1 | 11/2001 | Johnson | |
| 2011/0139723 | A1 | 6/2011 | Griffin et al. | |
| 2012/0265117 | A1 | 10/2012 | Fava et al. | |
| 2014/0287502 | A1 | 9/2014 | Taniguchi | |

FOREIGN PATENT DOCUMENTS

| | | |
|---|---|---|
| JP | 4307714 B2 | 8/2009 |
| JP | 2012-120456 A | 6/2012 |
| JP | 2012-210187 A | 11/2012 |
| WO | 2005/012480 A2 | 2/2005 |
| WO | 2013/061859 A1 | 5/2013 |

OTHER PUBLICATIONS

Written Opinion of the International Searching Authority, issued in PCT/JP2014/068936, dated Aug. 12, 2014.

* cited by examiner

METHOD FOR PRODUCING CELL CONCENTRATE, AND CELL SUSPENSION TREATMENT SYSTEM

CROSS REFERENCE TO RELATED APPLICATIONS

This application is a Divisional of copending application Ser. No. 14/906,320, filed on Jan. 20, 2016, which is a national phase of PCT International Application No. PCT/JP2014/068936 on Jul. 16, 2014, which claims the benefit under 35 U.S.C. § 119(a) to Patent Application No. 2013-152755, filed in Japan on Jul. 23, 2013, all of which are hereby expressly incorporated by reference into the present application.

TECHNICAL FIELD

The present invention relates to a technique of concentrating a cell suspension using a cell suspension treatment system including a cell suspension treatment device filled with a hollow fiber separation membrane.

BACKGROUND ART

In a field of cell medical treatment, when cells that are used in therapy are administered to a patient, the cells are administered to the patient immediately after the cells are sampled from a living body in some cases and are administered to the patient again after the cells are once cultured in vitro in other cases. The cells that are used in therapy are washed with a suspension appropriate for the therapy, are subjected to a cell preparation process such as concentration into a volume appropriate for administration, and then, are transplanted in general. The washing indicates replacement of body fluid, a culture medium, or the like in which the cells are suspended by physiological saline, infusion, or the like. Unnecessary impurities in a cell concentrate can be removed by performing washing treatment in which dilution and concentration are repeatedly performed on the cell concentrate, thereby preferably using the cell concentrate for transplantation into human and animals.

The cells that are used for the cell medical treatment are valuable and the cells capable of being obtained are limited in many cases. Therefore, loss of the cells in the cell preparation process should be minimized. Further, components mixed in the suspension need to be removed by washing as much as possible because the components possibly give an adverse effect on the therapy.

In view of the above-mentioned circumstances, preparation of the cells with reduced loss of the cells while mixing of unnecessary components in the cell suspension is minimized in the cell preparation process is an important object, which can influence treatment results thereafter.

As a cell preparation method, for example, concentration and washing operations using centrifugation have been known. In a method using the centrifugation, the cell suspension is stored in a sealed container and is made to settle by centrifugation for concentrating and washing the cells. Thereafter, the container is opened by a clean bench or the like and supernatant in the suspension is removed. In this case, there is a concern over a possibility that the cells are released to the atmosphere and quality thereof is deteriorated due to contamination or the like. Although a centrifugal operation in a closed system has been proposed (Patent Document 1) in order to cope with the concern, increases in device size and cost are concerned.

Further, as another cell preparation method, a method of concentrating and washing a cell suspension using a rotary membrane filter has been proposed (Patent Document 2). This method can reduce a device in size and simplify the device and enables cells to be handled aseptically in a circuit of a closed system. However, the above-mentioned Patent Document 2 discloses that in order to automatically perform concentration and washing steps, a weight of a storage container is measured by a weight scale and change in weight is fed back to step control so as to automatically perform the steps. However, with the control based on the change in weight, there are concerns over accuracy and responsiveness, a concern over accurate switching of the steps, and a concern over quality deficiency because concentration and washing of the cell suspension are not performed accurately.

In order to cope with the concerns, a filtrating and washing system using a filtrating unit has been proposed (Patent Document 3). The system is a system in order to reuse patient blood lost in a surgery or the like. Patent Document 3 discloses that a blood volume stored in a storage tank is kept within a constant range using a level sensor detecting a liquid level of blood stored in the storage tank in this system. In this method, air bubbles in the system are detected by an air bubble detector and the steps are controlled. Control is made based on the detection of the air bubbles in this manner, thereby rapidly grasping the liquid volume in the circuit accurately. With this, switching of the steps can be expected to be performed immediately and accurately. Meanwhile, the system is used for blood as a target and mixing of the air bubbles in blood treatment is harmful. Therefore, the system detecting air bubbles is not supposed to be applied to a concentration system for removing the unnecessary components and reducing the volume to be administered as objects in the cell preparation process. Further, in the concentration system targeted on the blood, hollow fibers are used as in the above-mentioned Patent Document. Alternatively, when a hollow fiber membrane is used, there are concerns over an adverse effect by mixing of the air bubbles on separation performance of the hollow fibers and washing efficiency depending on types of the hollow fibers.

CITATION LIST

Patent Literatures

Patent Document 1: JP-T No. 2007-524396
Patent Document 2: Japanese Patent No. 4307714
Patent Document 3: Japanese Patent No. 3012689

SUMMARY OF INVENTION

Technical Problem

An object of the present invention is to solve the above-mentioned problems in production of a cell concentrate using a hollow fiber separation membrane and to provide a method for producing the cell concentrate with high accuracy, reduced loss of cells, a reduced concern over contamination, and reduced damage on the cells.

Further, another object of the invention is to provide a cell suspension treatment system capable of producing the cell concentrate as described above efficiently.

Solution to Problem

As a result of enthusiastic study for achieving the above-mentioned objects, the inventors have found the following.

That is, a cell concentrate with a reduced concern over contamination of cells, reduced damage on the cells, and reduced loss of the cells can be produced efficiently by using a cell suspension treatment system including a cell suspension treatment device filled with a hollow fiber separation membrane, a container storing therein the cells, a device detecting a volume in the storage container or a tube communicating the storage container and the cell suspension treatment device, and a circuit that is connected so as to concentrate a cell suspension while circulating it between the storage container and the cell suspension treatment device, detecting the volume in the storage container or the tube communicating the storage container and the cell suspension treatment device, and controlling the concentration with the circulation, resulting in completion of the invention.

That is to say, the invention provides the following:

(1) A method for producing a cell concentrate using a cell suspension treatment system including:
- a storage container of a cell suspension, which has a solution inlet port, a circulation outlet port, and a circulation inlet port;
- a cell suspension treatment device for concentrating the cell suspension by separating liquid from the cell suspension by filtration, the device including a container having a cell suspension introduction port, a cell suspension lead-out port, and a filtrate outlet, which is filled with a hollow fiber separation membrane,
- a circulation circuit for concentrating the cell suspension while circulating the cell suspension between the storage container and the cell suspension treatment device, the circuit being constituted by an introduction communication tube communicating the circulation inlet port of the storage container and the cell suspension introduction port of the cell suspension treatment device and a lead-out communication tube communicating the cell suspension lead-out port of the cell suspension treatment device and the circulation outlet port of the storage container;
- a collection container of a cell concentrate obtained by concentration;
- a collection path for feeding the cell concentrate in the storage container, the cell suspension treatment device, and the circulation circuit to the collection container;
- an injection path for injecting a solution into the solution inlet port of the storage container; and
- a detecting unit for detecting a volume of the cell concentrate in the storage container or the introduction communication tube of the circulation circuit, the method including:

a) a step of storing the cell suspension in the storage container by supplying the cell suspension to the storage container through the solution inlet port;

b) a step of concentrating the cell suspension by feeding the cell suspension in the storage container to the cell suspension treatment device through the introduction communication tube of the circulation circuit, and then, circulating the cell suspension into the storage container through the lead-out communication tube of the circulation circuit;

c) a step of terminating the step b) by detecting the volume of the cell concentrate in the storage container or the introduction communication tube of the circulation circuit; and d) a step of feeding and collecting the cell concentrate in the storage container, the cell suspension treatment device, and the circulation circuit to the collection container through the collection path.

(2) The method for producing the cell concentrate, wherein the step b) and the step c) are further repeated after diluting the cell concentrate in the storage container by injecting a diluent into the storage container through the solution inlet port of the storage container after the step c).

(3) The method for producing the cell concentrate, wherein priming is performed by injecting priming liquid through the solution inlet port before the step a).

(4) The method for producing the cell concentrate, wherein the step a) and the step b) are executed in parallel.

(5) The method for producing the cell concentrate, wherein the detecting unit for detecting the volume in the circulation circuit is an air bubble sensor provided on the introduction communication tube of the circulation circuit.

(6) The method for producing the cell concentrate, wherein the detecting unit for detecting the volume in the storage container is one or more air bubble sensors provided on a circuit parallel with the storage container and communicating with a lower portion of the storage container.

(7) The method for producing the cell concentrate, wherein a chamber is provided on the circuit communicating with the lower portion of the storage container.

(8) The method for producing the cell concentrate, wherein an air bubble sensor is provided on the injection path.

(9) A cell suspension treatment system including:
- a storage container of a cell suspension, which has a solution inlet port, a circulation outlet port, and a circulation inlet port;
- a cell suspension treatment device for concentrating the cell suspension by separating liquid from the cell suspension by filtration, the device including a container having a cell suspension introduction port, a cell suspension lead-out port, and a filtrate outlet, which is filled with a hollow fiber separation membrane,
- a circulation circuit for concentrating the cell suspension while circulating the cell suspension between the storage container and the cell suspension treatment device, the circuit being constituted by an introduction communication tube communicating the circulation inlet port of the storage container and the cell suspension introduction port of the cell suspension treatment device and a lead-out communication tube communicating the cell suspension lead-out port of the cell suspension treatment device and the circulation outlet port of the storage container;
- a collection container for collecting a cell concentrate obtained by concentration;
- a collection path for feeding the cell concentrate in the storage container, the cell suspension treatment device, and the circulation circuit to the collection container;
- an injection path for injecting a solution into the solution inlet port of the storage container;
- a detecting unit for detecting a volume of the cell concentrate in the storage container or the introduction communication tube of the circulation circuit; and
- a controller that controls the detecting unit to detect concentration of the cell concentrate to a predetermined volume and terminates feeding of the cell concentrate to the cell suspension treatment device from the storage container.

(10) The cell suspension treatment system, wherein the detecting unit for detecting the volume in the circulation circuit is an air bubble sensor provided on the introduction communication tube of the circulation circuit.

(11) The cell suspension treatment system, wherein the detecting unit for detecting the volume in the storage container is an air bubble sensor provided on a circuit parallel with the storage container and communicating with a lower portion of the storage container.

(12) The cell suspension treatment system, wherein a chamber is provided on the circuit communicating with the lower portion of the storage container.

(13) The cell suspension treatment system, wherein an air bubble sensor is provided on the injection path.

(14) The cell suspension treatment system, wherein all the solution inlet port, the circulation outlet port, and the circulation inlet port are provided on a lower portion of the storage container.

(15) The cell suspension treatment system, wherein a ventilation hole is provided in the vicinity of an upper portion of the storage container and an inner portion of the storage container is an atmospheric opening system.

Advantageous Effects of Invention

In the invention, the cell concentrate with reduced damage on cells, reduced loss of the cells, and a reduced concern over contamination can be produced aseptically in a closed system with high accuracy by using the cell suspension treatment system including the cell suspension treatment device filled with the hollow fiber separation membrane, the container storing therein the cells, the circuit connecting the storage container and the cell suspension treatment device, and the device detecting the volume in the storage container or the tube communicating the storage container and the cell suspension treatment device, detecting concentration of the cell concentrate to a predetermined volume by the detecting unit, and terminating feeding of the cell concentrate to the cell suspension treatment device from the storage container. Therefore, the concentrated cells can be provided for cell medical treatment. Further, the cell concentrate can be produced efficiently even when treatment conditions are previously programmed into the cell suspension treatment system so as to automate production of the cell concentrate.

In the method for producing the cell concentrate, after the cell concentrate in the storage container is diluted by injecting the diluent into the storage container after the cell concentration, the concentration step b) and the concentration termination step c) are further repeated. With this, unnecessary components in the cell concentrate are removed, thereby obtaining a cell concentrate with higher purity.

In the method for producing the cell concentrate, the priming is performed by injecting the priming liquid through the solution inlet port before the storage step a). With this, cell concentration can be performed with preferable operability.

In the method for producing the cell concentrate, the storage step a) and the concentration step b) are executed in parallel. This can shorten treatment time.

In the cell suspension treatment system, the detecting unit for detecting the volume in the circulation circuit is the air bubble sensor provided on the introduction communication tube of the circulation circuit. With this, the cell suspension can be further concentrated in comparison with the case where the volume in the storage container is detected. Therefore, a volume of the concentrated suspension can be reduced, thereby reducing an amount of unnecessary components in the suspension.

Further, the detecting unit for detecting the volume in the storage container is one or more air bubble sensors provided on the circuit parallel with the storage container and communicating with the lower portion of the storage container. With this, a compact air bubble sensor that detects the liquid level in the circuit as a small range can be used although an air bubble sensor that detects the liquid level in a large range is required in the case of detecting the liquid level in the storage container.

The chamber is provided on the circuit communicating with the lower portion of the storage container. With this, generation of failures that are detected by the air bubble sensor can be reduced even when air bubbles enter the circuit mistakenly.

Further, the air bubble sensor is provided on the injection path. With this, even when a treatment amount of the target cell suspension is not known previously, the air bubble sensor detects air bubbles that have entered the injection path after the cell suspension runs out. Therefore, the target of a total volume can be treated without setting driving time of a pump for each treatment.

In addition, all the solution inlet port, the circulation outlet port, and the circulation inlet port are provided on the lower portion of the storage container. With this, the cell suspension and the solution for dilution that are supplied to the storage container through the solution inlet port are mixed and stirred with liquid circulating in the storage container and the circulation circuit efficiently, thereby performing concentration and dilution efficiently.

Further, one or more ventilation holes are provided in the vicinity of the upper portion of the storage container and the inner portion of the storage container is the atmospheric opening system. Therefore, when the container is vacuumed in order to discharge the liquid in the storage container, crush of the storage container can be prevented.

DESCRIPTION OF EMBODIMENTS

A method for producing a cell concentrate according to the invention uses a cell suspension treatment system including a storage container of a cell suspension, which has a solution inlet port, a circulation outlet port, and a circulation inlet port, a cell suspension treatment device for concentrating the cell suspension by separating liquid from the cell suspension by filtration, the device including a container having a cell suspension introduction port, a cell suspension lead-out port, and a filtrate outlet, which is filled with a hollow fiber separation membrane, a circulation circuit for concentrating the cell suspension while circulating the cell suspension between the storage container and the cell suspension treatment device, the circuit being constituted by an introduction communication tube communicating the circulation inlet port of the storage container and the cell suspension introduction port of the cell suspension treatment device and a lead-out communication tube communicating the cell suspension lead-out port of the cell suspension treatment device and the circulation outlet port of the storage container, a collection container of a cell concentrate obtained by concentration, a collection path for feeding the cell concentrate in the storage container, the cell suspension treatment device, and the circulation circuit to the collection container, an injection path for injecting a solution into the solution inlet port of the storage container, and a detecting unit for detecting a volume of the cell concentrate in the storage container or the introduction communication tube of the circulation circuit.

First, the cell suspension treatment system will be described.

(Storage Container)

The storage container that is used in the cell suspension treatment system is a container storing therein a cell suspension to be treated and circulating and storing a cell concentrate obtained by feeding the cell suspension to the cell suspension treatment device as will be described later. The storage container has the solution inlet port, the circulation outlet port, and the circulation inlet port.

The solution inlet port is a port for supplying the cell suspension into the storage container. The circulation inlet port is a port for feeding the cell suspension to the cell suspension treatment device from the storage container and the circulation outlet port is a port for feeding the cell concentrate obtained by concentration in the cell suspension treatment device to the storage container.

These ports are preferably installed on the lower portion of the storage container. The cell suspension and a solution for dilution that are supplied through the solution inlet port are stirred with liquid circulating in the storage container and the circulation circuit efficiently by installing all these ports on the lower portion. With this, concentration and dilution can be performed efficiently.

Although it is sufficient that the number of each of the solution inlet port, the circulation outlet port, and the circulation inlet port is one, a plurality of them may be provided if necessary. For example, although the solution inlet port can be used not only for the cell suspension but also as a port for a diluent and priming liquid, inlet ports for the diluent and the priming liquid may be provided in addition to the port for the cell suspension.

A port for another object may be provided in addition to the ports of the above-mentioned three types. For example, a collection port for feeding the cell concentrate to the collection container may be provided. The collection port of the storage container and the collection container are directly connected to each other, so that the cell concentrate in the storage container can be collected rapidly.

As a material of the storage container, although any material may be used as long as it does not influence cells in the cell suspension or the cell concentrate, the material is preferably flexible plastic in terms of preferable handling property.

The inner surfaces of the storage container on which satin finish processing has been performed are advantageous because residual liquid when the suspension is discharged from the storage container can be reduced.

A capacity of the storage container is not particularly limited for use. However, when the capacity of the storage container is too large, a large volume of diluent that is used for dilution is required. Therefore, the capacity of the storage container is preferably 1000 mL or less.

It is sufficient that the shape of the storage container and the structures, the materials, and the like of the respective ports are appropriately determined based on a type of the cell suspension to be treated and the capacity of the storage container, and they are not particularly limited.

The ventilation hole may be provided on the upper portion of the storage container. With provision of the ventilation hole, an atmospheric opening system in which the air in the storage container and the atmosphere can be exchanged is realized. For example, this provides an advantage that when the liquid in the storage container is discharged, crush of the storage container due to vacuum of the inner portion of the storage container can be prevented. An air filter may be provided in the ventilation hole so as to prevent unnecessary components from being mixed into the storage container from the outside.

(Cell Suspension Treatment Device)

The cell suspension treatment device is a device for concentrating the cell suspension by separating liquid from the cell suspension by filtration and is connected such that the cell suspension can be fed thereto from the storage container.

The cell suspension treatment device includes the container having the cell suspension introduction port, the cell suspension lead-out port, and the filtrate outlet, which is filled with the hollow fiber separation membrane.

The cell suspension introduction port is an inlet for introducing the cell suspension into the cell suspension treatment device from the storage container and is connected to the circulation inlet port of the storage container.

The cell suspension lead-out port is an outlet for taking out the cell suspension (cell concentrate) subjected to the concentration treatment. In the invention, the cell suspension lead-out port is connected to the circulation outlet port of the storage container. With this, the cell suspension can be concentrated while being circulated between the storage container and the cell suspension treatment device.

The filtrate outlet is an outlet for taking out the liquid separated from the cell suspension by filtration.

As the hollow fiber separation membrane that is used for the cell suspension treatment device, the hollow fiber separation membrane formed by bundling several tens to several thousands of hollow fibers is filled into a cylindrical container preferably. In the invention, the hollow fiber separation membrane may be arranged in a linear form, a deflection form, or a spiral form. The shape of the hollow fiber separation membrane is not particularly limited as long as both ends of the hollow fiber separation membrane are held between the cell suspension inlet and the cell suspension outlet.

As the hollow fiber separation membrane that is used for the cell suspension treatment device, synthetic polymer materials can be used in terms of safety, stability, and the like of the materials. Among them, a polysulfone-based, polyolefine-based, or cellulose-based polymer material can be preferably used. Further, a hole diameter of the hollow fiber separation membrane can be arbitrarily set as long as the cells do not leak out to the outside therethrough but a large hole diameter as much as possible is preferable in order to efficiently separate unnecessary components by filtration. To be specific, the hollow fiber separation membrane having an average hole diameter of 0.01 µm or more to 1.0 µm or less can be preferably used. The hollow fibers having an inner diameter of 400 µm or more to 1000 µm or less can be preferably used.

When the cell suspension supplied through the cell suspension introduction port passes through the inner side of the hollow fiber separation membrane, the liquid is separated to the outside of the hollow fiber separation membrane by filtration, so that the cell concentrate is produced.

The cell suspension treatment device has the following configuration, for example. That is, the cylindrical container is filled with the hollow fiber separation membrane, end portions of the hollow fibers are made to closely adhere to end portions of the cylindrical container with an adhesive or the like. Header portions forming the cell suspension introduction port and the cell suspension lead-out port are provided on the end portions of the cylindrical container such that the cell suspension can flow in and flow out from the hollow fiber membrane opened on the end portions. It is sufficient that one or more filtrate outlets are provided on the cylindrical container and a filtrate separated through the inner side of the hollow fibers by filtration is discharged through the filtrate outlet. The cell suspension treatment device is required to have a configuration in which the hollow fiber separation membrane is filled into the sealed container. However, various configurations can be employed as long as it has the configuration in which the cell suspension introduction port and the cell suspension lead-out port are separated from the filtrate outlet with a wall material forming the hollow fiber separation membrane. For example, a dialyzer that is used for hemodialysis and the like can be exemplified as a similar configuration.

A circuit for causing the filtrate separated by filtration with the hollow fiber separation membrane to flow out is installed on the filtrate outlet of the cell suspension treatment device. Coupling of the circuit for the filtrate and a waste liquid container is preferable because a concern over leakage of the filtrate to the outside can be reduced.

The filtrate taken out from the filtrate outlet can be collected by being fed to the waste liquid container or the like. The waste liquid container can be used without being particularly limited as long as it is a container causing no leakage of the waste liquid.

A pump for feeding the filtrate may be installed between the filtrate outlet of the cell suspension treatment device and the waste liquid container or may not be installed. For example, the filtrate can be discharged at a constant flow rate by providing the pump on a path connecting the filtrate outlet and the waste liquid container, thereby making treatment time constant. With this, filtration efficiency in the cell suspension treatment device can be controlled. That is to say, the filtrate is accelerated to be discharged from the cell suspension treatment device by driving the pump. As a result, the concentration treatment in the cell suspension treatment device can be accelerated.

Further, when the cell concentrate obtained by concentration to a predetermined concentration is fed to the collection container so as to be collected, the pump is stopped. This enables the collection to be performed rapidly.

The collected filtrate may be discarded as it is or may be reused as a diluent of a cell culture liquid by being subjected to reprocessing such as sterilization processing.

Further, a cell concentrate collection port for feeding the cell concentrate in the cell suspension treatment device to the collection container may be provided on the cell suspension treatment device in addition to the cell suspension introduction port, the cell suspension lead-out port, and the filtrate outlet. It is sufficient that the cell concentrate collection port is connected to the collection container.

(Circulation Circuit)

The circulation circuit is a circuit constituted by the introduction communication tube communicating the circulation inlet port of the storage container and the cell suspension introduction port of the cell suspension treatment device and the lead-out communication tube communicating the cell suspension lead-out port of the cell suspension treatment device and the circulation outlet port of the storage container.

In the invention, the cell suspension is concentrated while being circulated between the storage container and the cell suspension treatment device through the circulation circuit so as to produce the cell concentrate.

A tube made of common plastic can be preferably used as the tubes constituting the circulation circuit. Vinyl chloride can be preferably used in terms of safety and durability.

A pump is preferably installed on the circulation circuit in terms of control easiness of the circulation of the cell suspension or the cell concentrate. The number of pumps is not particularly limited and one pump is sufficient in terms of control easiness. As a position of the pump, it is sufficient that the pump is installed on either of the introduction communication tube or the lead-out communication tube. Installation of the pump on the introduction communication tube is preferable because a high-pressure solution can be introduced to the cell suspension introduction port of the cell suspension treatment device and the liquid can be separated efficiently.

In the invention, a branch portion may be provided at an arbitrary position on the circulation circuit. The branch portion is coupled to the collection container through a tube, so that the cell concentrate in the storage container, the cell suspension treatment device, and the circulation circuit can be collected into the collection container rapidly while a path from the branch portion to the collection container is used as a final collection path. Installation of the branch portion at a position closer to the circulation outlet port as much as possible is preferable because a residue liquid remaining in the circulation circuit from the branch portion to the outlet port can be reduced in a collection treatment.

(Collection Container)

The collection container is a container for collecting therein the cell concentrate obtained by concentration to the predetermined concentration.

It is sufficient that the collection container is a container made of flexible plastic. The inner surfaces of the collection container on which satin finish processing has been performed are advantageous because residual liquid after collection of the cell concentrate can be reduced. Further, the collection container may have a connection port to which a needle, a syringe, or the like can be connected. This configuration enables the collection container to be preferably used when the cell concentrate collected in the collection container is transferred to another container. The shape of the collection container is not particularly limited. For example, the shape of the collection container having a small capacity of the inner portion thereof is preferable for the following reason. That is, when the capacity is large, the inner area of the container with which collected cells make contact is increased and the cells that have adhered thereto remain in the container, resulting in loss of the cells.

(Collection Path)

The collection path is a path for feeding the cell concentrate in the storage container, the cell suspension treatment device, and the circulation circuit to the collection container. As a tube forming the collection path, a tube made of common plastic can be used. In particular, a tube made of vinyl chloride can be preferably used in terms of safety and durability.

The following three modes of the collection path can be employed.

1) When the branch portion is provided on the circulation circuit, a path coupling the branch portion and the collection container corresponds to the collection path.

2) When the collection port of the storage container and the collection container are connected, the connected path corresponds to the collection path.

3) When the cell concentrate collection port of the cell suspension treatment device and the collection container are connected, the connected path corresponds to the collection path.

Although it is sufficient that the collection path of any one of the above-mentioned modes is employed, two or more modes may be employed in combination.

(Injection Path)

The injection path is a path for injecting a solution into the solution inlet port of the storage container. As a tube forming the injection path, a tube made of common plastic can be used. In particular, a tube made of vinyl chloride can be preferably used in terms of safety and durability.

The solution in the invention includes a diluent for again diluting the cell concentrate obtained by concentrating the cell suspension and priming liquid for priming the entire cell suspension treatment system before the concentration treatment in addition to the cell suspension.

Examples of the diluent that is used in the invention include physiological saline, infusion, distilled water, a buffer solution, a culture medium, plasma, and liquids containing inorganic salts, saccharides, serum, and protein. In particular, the physiological saline or the infusion can be preferably used in terms of safety. Further, examples of the priming liquid also include physiological saline, infusion, distilled water, a buffer solution, a culture medium, plasma, and liquids containing inorganic salts, saccharides, serum, and protein. In particular, the physiological saline and the infusion can be preferably used in terms of safety. In the invention, the same solution or different solutions may be used as the diluent and the priming liquid. When different solutions are used, circuits that are separated from the branch portion on the circuit connected to the solution inlet port of the storage container and are coupled to the respective connection portions can be installed.

Further, the other end portions of the injection path that is connected to the solution inlet port of the storage container are connection portions for a cell culture bag and a diluent bag and/or a priming liquid bag.

A bottle needle, a male luer, a female luer, lock connection, or the like can be used for the cell culture bag connection portion with no particular limitation as long as it has a shape capable of being connected to a bag that is used for cell culture.

A bottle needle, a male luer, a female luer, lock connection, or the like can be used for the diluent bag connection portion or the priming liquid bag connection portion with no particular limitation as long as it has a shape capable of being connected to a bag storing therein the diluent or the priming liquid.

A pump for feeding the liquid is preferably installed on the injection path. The pump can feed the liquid to the storage container stably. A position at which the pump is installed is preferably a position on the circuit coupling a junction place of the circuits coupled to the cell culture bag connection portion, the diluent bag connection portion, and the priming liquid bag connection portion, and solution inlet port in terms of a point that the number of pumps necessary for feeding the liquid can be reduced.

(Detecting Unit)

The detecting unit is a unit for detecting the volume of the cell concentrate in the storage container or the introduction communication tube of the circulation circuit.

An air bubble sensor that directly detects a liquid level of storage liquid in the storage container can be used as the unit for detecting the volume in the storage container.

The following another mode may be employed, for example. That is, a tube is installed in parallel with the storage container in the up-down direction so as to form a circuit in which the storage container and the tube communicate with each other on a lower portion, the liquid level in the tube is adjusted to be equal to the liquid level in the storage container, and an air bubble sensor is installed on the tube. With this means, the air bubble sensor can detect the liquid level in the tube as the liquid level in the storage container.

Moreover, a chamber may be provided on a lower portion of the tube installed on parallel with the storage container. In particular, a chamber having a larger inner diameter than that of the tube is installed. With this, generation of failures detected due to undesirable entrance of air bubbles into the tube installed in parallel can be expected to be reduced.

The air bubble sensor may be provided on the introduction communication tube communicating with the circulation inlet port of the storage container as the unit for detecting the volume of the cell concentrate in the introduction communication tube. This mode has advantages that a volume of the concentrated suspension (cell concentrate) can be reduced and an amount of unnecessary components in the suspension can be reduced because the cell suspension can be further concentrated in comparison with the unit for detecting the volume in the storage container.

Further, although the position of the air bubble sensor that is installed on the introduction communication tube is not particularly limited, the circuit connecting the storage container and the air bubble sensor can be shortened by installing the air bubble sensor at a position close to the storage container.

In the cell suspension treatment system of the invention, the air bubble sensor may be installed on the injection path connected to the solution inlet port of the storage container. When the air bubble sensor detects air bubbles, storage of the solution such as the cell suspension, the diluent, and the priming liquid in the storage container can be terminated. For example, installation of the air bubble sensor on the injection path provides an advantage that even when a treatment amount of the target cell suspension is not known, the target of a total volume can be treated without setting driving time of the pump for each treatment. Further, a step of adding the solution of a constant volume based on the driving time of the pump can be executed. For example, when only a part of the cell suspension is required to be treated, a part of the cell suspension can be treated by setting the driving time of the pump. Although the air bubble sensor can be installed at an arbitrary position on the injection path, the air bubble sensor is advantageously installed at a position closer to the storage container as much as possible in terms of a point that a residual volume in the injection path is reduced.

Moreover, another air bubble sensor may be provided on an upper portion of the storage container. The installation of the air bubble sensor enables presence and absence of the solution in the vicinity of the upper portion in the storage container to be determined. That is to say, when the liquid of a volume exceeding the capacity of the storage container is supplied, the sensor detects it and can notify a user of it as warning.

A commonly used pump and air bubble sensor can be used for those that are used in the cell suspension treatment system in the invention. Further, a flow path can be switched by providing a clamp at a desired position on the circuit. For example, the pumps, the air bubble sensors, and the clamp are not particularly limited and those that are used for a dialysis machine and the like may be used.

In the cell suspension treatment system, the detecting unit detects concentration of the cell concentrate to the predetermined volume and the controller terminating the feeding of the cell concentrate to the cell suspension treatment device from the storage container terminates the concentration.

When the cell suspension is concentrated using the cell suspension treatment device as in the invention, entrance of the air into the cell suspension treatment device causes a problem that not only concentration capability is lowered but also cells adhere to the inner portion of the cell suspension treatment device when the cells are collected and loss of the cells is largely increased. As a unit that determines a termination time point of the concentration step, a method in which a volume of the liquid to be fed to the cell suspension treatment device and a volume of waste liquid to be discarded from the cell suspension treatment device are determined previously is considered. However, even when the liquid feeding volumes of the pumps installed on the circuit and the path in the cell suspension treatment system, or the like, are adjusted actually, the degree of concentration in the cell suspension treatment device is not constant depending on the concentrations of the cell suspension, the sizes of the cells, the types of the cells, and the like, and the concentration is undesirably performed until the air enters the cell suspension treatment device in some cases. For this reason, a state of the cell suspension treatment device needs to be monitored during the concentration and atomization has been difficult.

In contrast, in the invention, the termination of the concentration step of the cell suspension is determined using the detecting unit. With this, the air does not enter the cell suspension treatment device regardless of the states and the like of the cell suspension and sufficiently concentrated cell concentrate can be obtained with high accuracy.

Hereinafter, an example of the cell suspension treatment system will be described with reference to the drawings.

Figure 1:
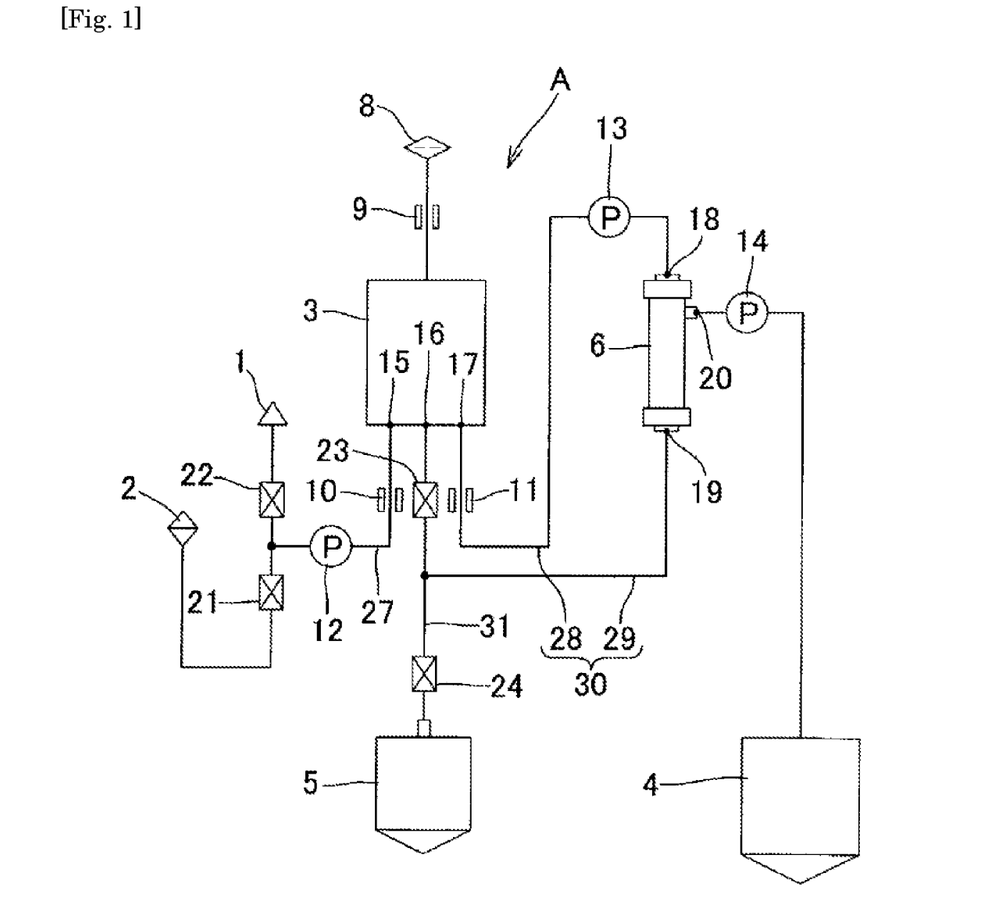
FIG. 1 is a descriptive view illustrating one embodiment of a cell suspension treatment system A of the invention.

FIG. 1 is a circuit diagram of a system including the detecting unit for detecting the volume of the cell concentrate in the introduction communication tube of the circulation circuit as one embodiment of a cell suspension treatment system A that is used in the invention.

The cell suspension treatment system A in FIG. 1 includes an injection path 27 a leading end of which is branched. The branched end portions correspond to a cell culture bag connection portion 1 and a diluent bag connection portion 2, respectively. Clamps 22 and 21 are provided on the injection path 27 at the storage container 3 side relative to the cell culture bag connection portion 1 and the diluent bag connection portion 2. A solution that is supplied to the storage container 3 from the cell culture bag connection portion 1 or the diluent bag connection portion 2 can be switched by opening and closing the clamps 22 and 21.

Further, a pump 12 is provided on the injection path 27 at the storage container 3 side relative to the branch portion. A supply volume of the solution to the storage container 3 can be adjusted by adjusting the driving speed of the pump 12.

An air bubble sensor 10 is installed on the injection path 27 at the storage container 3 side relative to the pump 12. When the solution that is supplied runs out and the air bubble sensor 10 detects the air that has entered the injection path 27, the supply of the solution to the storage container 3 can be stopped at an optimum timing by stopping the pump 12. Further, when the pump 12 and the air bubble sensor 10 are electrically connected to each other, the supply of the solution can be adjusted automatically.

The other end of the injection path 27 is connected to a solution inlet port 15 on a lower portion of the storage container 3.

A circulation outlet port 16 and a circulation inlet port 17 are arranged on the lower portion of the storage container 3 in addition to the solution inlet port 15 and an air filter 8 is provided above the storage container 3 so as to make a pressure of an inner portion of the storage container 3 to an atmospheric pressure. Further, an air bubble sensor 9 is installed on a path from the storage container 3 to the air filter 8 so as to detect supply of the solution of a volume equal to or larger than the capacity of the storage container 3. The air bubble sensor 9 is electrically connected to the pump 12, so that supply of the solution can be stopped automatically.

The circulation inlet port 17 is connected to a cell suspension introduction port 18 on an upper portion of a cell suspension treatment device 6 through an introduction communication tube 28. An air bubble sensor 11 is installed on the introduction communication tube 28 and a pump 13 is installed at the cell suspension treatment device 6 side relative to the air bubble sensor 11. The solution in the storage container 3 can be supplied to the cell suspension treatment device 6 by driving the pump 13. When the solution that is supplied to the cell suspension treatment device 6 from the storage container 3 runs out and the air bubble sensor 11 detects the air that has entered the introduction communication tube 28, the supply of the solution can be stopped at an optimum timing without causing the air to enter the cell suspension treatment device 6 by stopping the pump 13. Further, when the pump 13 and the air bubble sensor 11 are electrically connected to each other, the supply of the solution can be adjusted automatically.

The cell suspension treatment device 6 is filled with the hollow fiber separation membrane (not illustrated). Liquid of the cell suspension supplied through the cell suspension introduction port 18 is separated when the cell suspension passes through the hollow fiber separation membrane. The separated liquid is discharged through a filtrate outlet 20 provided on the upper side surface of the cell suspension treatment device 6.

The filtrate outlet 20 is connected to a waste liquid container 4 through a tube and a pump 14 for prompting discharge of the filtrate and concentration with the hollow fiber separation membrane is provided on the tube.

A cell suspension lead-out port 19 on a lower portion of the cell suspension treatment device 6 is connected to the circulation outlet port 16 through a lead-out communication tube 29. A clamp 23 is provided on the lead-out communication tube 29 and circulation of the cell concentrate obtained by concentration in the cell suspension treatment device 6 to the storage container 3 can be adjusted by opening and closing the clamp 23.

The introduction communication tube 28 and the lead-out communication tube 29 constitute a circulation circuit 30 that circulates the cell suspension and the cell concentrate between the storage container 3 and the cell suspension treatment device 6.

A branch portion is provided on the lead-out communication tube 29 at the cell suspension treatment device 6 side relative to the clamp 23 and the branch portion and a collection container 5 are connected through a collection path 31. A clamp 24 is provided on the collection path 31. The clamp 24 is closed while the circulation and the concentration using the circulation circuit 30 are performed as described above. When the cell concentrate is collected, the cell concentrate can be supplied to the collection container 5 by opening the clamp 24.

Figure 2:
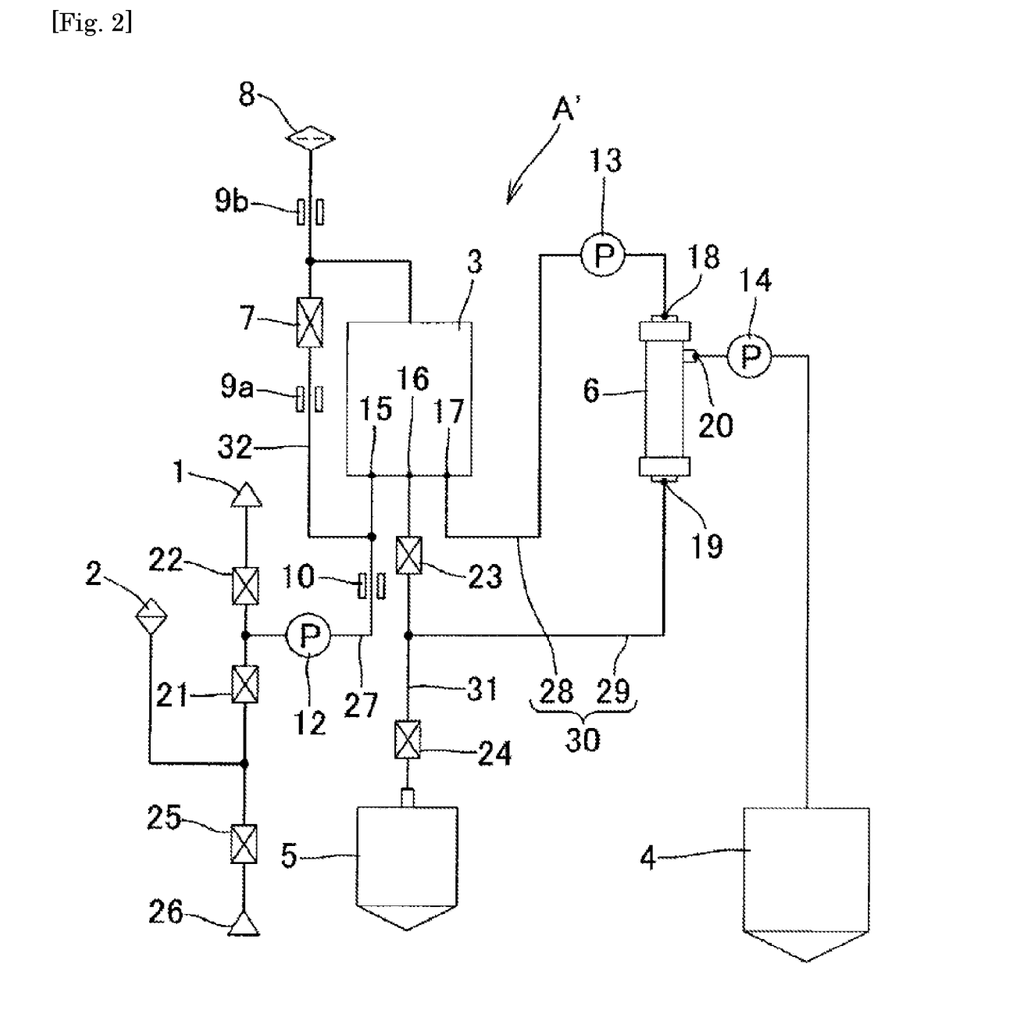
FIG. 2 is a descriptive view illustrating an embodiment of another cell suspension treatment system A' of the invention.

FIG. 2 is a circuit diagram of a system including the detecting unit for detecting the volume of the cell concentrate in the storage container as another embodiment of a cell suspension treatment system A' that is used in the invention.

In the cell suspension treatment system A' as illustrated in FIG. 2, the injection path 27 includes a priming liquid bag connection portion 26 in addition to the cell culture bag connection portion 1 and the diluent bag connection portion 2. The priming liquid bag connection portion 26 corresponds to the other end of a branch portion provided on the injection path 27 at the storage container 3 side relative to the diluent bag connection portion 2. A clamp 25 is provided between the priming liquid bag connection portion 26 and the branch portion. Supply of the priming liquid to the storage container 3 can be adjusted by opening and closing the clamp 25.

Another branch portion is provided at the storage container 3 side relative to the air bubble sensor 10 provided on the injection path 27. A circuit 32 communicating the branch portion and the upper portion of the storage container 3 is provided. With the circuit 32, when the storage container 3 is filled with the solution, the liquid level in the storage container 3 and the liquid level of the solution in the circuit 32 are in parallel through the injection path 27. An air bubble sensor 9*a* is installed at a desired height of the circuit 32. With this, even a compact air bubble sensor that detects the liquid level in the circuit 32 as a small range can detect the liquid level of the solution in the storage container 3 although an air bubble sensor that detects the liquid level in a large range is required when the air bubble sensor is directly provided on the storage container 3.

Further, in the invention, the cell suspension and the like are circulated between the storage container 3 and the cell suspension treatment device 6 by the pump 13 installed on the introduction communication tube 28 for concentration. If the circuit 32 is coupled to the introduction communication tube 28, it tends to be difficult to accurately measure the liquid level even by the air bubble sensor 9*a* on the circuit 32 due to pulsation of the pump 13.

Unlike this configuration, connection of the circuit 32 to the injection path 27 as the different path from the introduction communication tube 28 as described above also provides an advantage that the liquid level in the circuit 32 can be accurately measured as the liquid level in the storage container 3.

Although shake of the liquid level can be suppressed by using a tube having a small hole diameter for a tube forming the circuit 32, the hole diameter thereof is not particularly limited.

A chamber 7 may be provided on the circuit 32 at a higher position than the air bubble sensor 9*a*. The provision of the chamber 7 gives an advantage that the shake of the liquid level can be suppressed in comparison with the case of the circuit 32 alone.

It is sufficient that a branch portion is provided on the circuit 32 at a higher position than the upper portion of the storage container 3 and the air filter 8 is provided at a higher position than the branch portion in the same manner as FIG. 1. Further, another air bubble sensor 9*b* may be provided between the branch portion and the air filter 8. With this configuration, even when the cell suspension of a volume exceeding the capacity of the storage container 3 is supplied, the air bubble sensor 9*b* operates to stop the pump 12, thereby suppressing leakage of the cell suspension from the air filter 8. The air bubble sensor 9*b* is electrically connected to the pump 12, so that automatic treatment can be performed.

Other configurations of the cell suspension treatment system A' as illustrated in FIG. 2 are the same as those in FIG. 1 and description thereof is therefore omitted.

Figure 3:
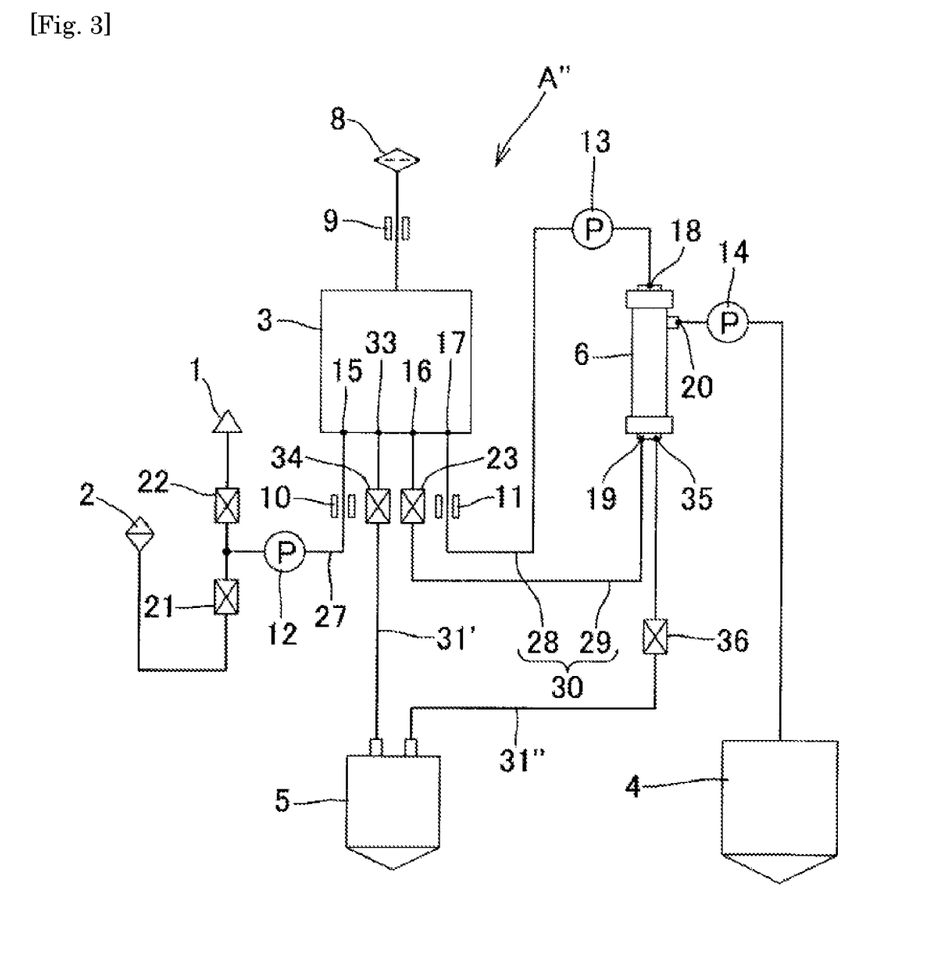
FIG. 3 is a descriptive view illustrating an embodiment of still another cell suspension treatment system A" of the invention.

The collection path 31 may employ a mode in a cell suspension treatment system A" as illustrated in FIG. 3.

That is to say, a collection port 33 may be provided on the storage container 3 and a collection path 31' connecting the collection port 33 and the collection container 5 may be formed. It is sufficient that a clamp 34 is provided on the path.

Further, a cell concentrate collection port 35 may be provided on the cell suspension treatment device 6 and a collection path 31" connecting the cell concentrate collection port 35 and the collection container 5 may be formed. It is sufficient that a clamp 36 is also provided on the path.

(Method for Producing Cell Concentrate)

A method for producing a cell concentrate according to the invention uses the cell suspension treatment system having the above-mentioned configuration and includes:

a) a step of storing the cell suspension in the storage container by supplying the cell suspension to the storage container through the solution inlet port;

b) a step of concentrating the cell suspension by feeding the cell suspension in the storage container to the cell suspension treatment device through the introduction communication tube of the circulation circuit, and then, circulating the cell suspension into the storage container through the lead-out communication tube of the circulation circuit;

c) a step of terminating the step b) by detecting the volume of the cell concentrate in the storage container or the introduction communication tube of the circulation circuit; and d) a step of feeding and collecting the cell concentrate in the storage container, the cell suspension treatment device, and the circulation circuit to the collection container through the collection path.

A specific example of production of the cell concentrate using the cell suspension treatment system as illustrated in FIG. 1 will be described below. It is assumed that the respective clamps are closed previously before the production.

Step a) (Storage Step)

First, the cell culture bag connection portion 1 is connected to a cell culture bag and the diluent bag connection portion 2 is connected to a diluent bag. Then, it is checked that the clamp 22 is opened and the clamp 21 is closed. The pump 12 is driven so as to cause the cell suspension to be stored in the storage container 3 from the cell culture bag connection portion 1 at a predetermined flow rate. A volume of the cell suspension to be stored is not particularly limited as long as the volume does not exceed the capacity of the storage container. The flow rate is preferably in a range of 50 mL/min to 300 mL/min.

Step b) (Concentration Step)

Subsequently, the clamp 23 is opened and liquid components such as a culture medium are separated from the cell suspension by filtration using the hollow fiber membrane so as to concentrate the cell suspension while the cell suspension is made to pass through the circulation circuit 30 between the storage container 3 and the cell suspension treatment device 6 for circulation using the pump 13. A circulation direction at this time is a direction in which the cell suspension flows to the cell suspension introduction port 18 of the cell suspension treatment device 6 from the circulation inlet port 17 of the storage container 3. As a method of concentrating the cell suspension, either of filtration using a pressure of the liquid flowing through the inner side of the hollow fiber separation when the cell suspension flows through the inner side or filtration using the pump 14 may be used.

The storage step and the concentration step may be repeatedly performed until the volume in the cell suspension bag coupled to the cell culture bag connection portion 1 becomes a predetermined volume or may be performed in parallel at the same time. Further, the cell suspension in the cell suspension bag may be treated to a constant volume based on the driving time of the pump 12 or feeding of the cell suspension by the pump 12 may be controlled by detecting, by the air bubble sensor 10, air bubbles flowing into the injection path 27 after the total volume of the cell suspension is fed.

Step c) (Concentration Termination Step)

After the cell suspension is concentrated until the air bubble sensor 11 provided on the introduction communication tube 28 detects air bubbles, the pumps 13 and 14 are stopped so as to terminate the concentration. In the cell suspension treatment system A as illustrated in FIG. 1, the concentration with high accuracy until the cell concentration in the storage container 3 runs out can be executed.

Step d) (Collection Step)

Thereafter, the clamp 23 is closed and the clamp 24 is opened. With this, sufficiently concentrated cell suspension in the storage container 3, the cell suspension treatment device 6, and the circulation circuit 30 can be collected into the collection container 5 after passing through the collection path 31.

In the invention, priming may be performed before the step a). In this case, the clamp 21 is opened and the clamp 22 is closed. With this, physiological saline as the priming liquid is stored in the storage container 3 from the diluent bag connection portion 2. The physiological saline is stored in the storage container 3 at a predetermined flow rate by driving the pump 12. A volume thereof that is stored is not particularly limited as long as the physiological saline of such a volume that the circulation circuit 30 and the cell suspension treatment device 6 are made to soak in the physiological saline is stored. The flow rate is preferably in a range of 50 mL/min to 300 mL/min.

Then, it is checked that the clamp 23 is opened and the clamp 24 is closed. The pump 13 installed on the introduction communication tube 28 of the circulation circuit 30 to which the storage container 3 and the cell suspension treatment device 6 are coupled and the pump 14 installed on the path connected to the filtrate outlet 20 are driven, so that priming in the circulation circuit 30 and the cell suspension treatment device 6 is performed. The circulation circuit 30 is filled with the priming liquid at a predetermined flow rate by the pump 13, and then, the pump 14 is driven so as to separate the priming liquid to the outside of the hollow fiber separation membrane by filtration and fill the cell suspension treatment device 6 with the priming liquid. In this case, the circulation direction may be either of the forward direction or the backward direction without being particularly limited. The flow rate of the pump 14 can be set without being particularly limited as long as it is lower than the flow rate of the pump 13. If the flow rate of the pump 14 is higher than the flow rate of the pump 13, a state where the circulation circuit 30 is not filled with the liquid can be possibly made and it is not preferable. The flow rate of the pump 13 is preferably adjusted in a range of 50 mL/min to 500 mL/min.

The cell concentration can be performed with preferable operability by performing the above-mentioned priming previously.

In the invention, after the concentration of the cell suspension is terminated in the step c), the cell suspension in the storage container 3 may be diluted by opening the clamp 21, closing the clamp 22, and feeding the diluent into the storage container 3 by the pump 12 (dilution step). After unnecessary components in the cell suspension are diluted in the dilution step, concentration is performed in the step b) again, and then, the concentration is terminated in the step c). With this, unnecessary components in the cell suspension are separated and removed by filtration with the hollow fiber membrane, thereby producing the cell concentrate with the unnecessary components further removed. It should be noted that the dilution step may be repeated by twice or more.

Air bubbles have entered the introduction communication tube 28 after the step c) to a position of the air bubble sensor 11. Therefore, the pump 13 is driven in the backward direction and the liquid level of the cell concentrate is returned to a position in the vicinity of the circulation inlet port 17 on the lower portion of the storage container 3 or a position in the storage container 3 so as to prevent the air bubbles from entering the cell suspension treatment device 6 even when the step b) is performed again.

When the priming liquid and the diluent are different in the case where the priming and the dilution are performed, it is sufficient that the bag storing therein the priming liquid and the bag storing therein the diluent are exchanged.

Further, the storage step in the step a) and the concentration step in the step b) may be executed in parallel. There is an advantage that the treatment time can be shortened by executing the step a) and the step b) in parallel.

A specific example of production of a cell concentrate in the case using the cell concentration treatment system A' as illustrated in FIG. 2 will be described below.

The storage step in the step a) can be processed in the same manner as the case using the cell concentration treatment system A as illustrated in FIG. 1. However, when the priming is performed before the step a) using the cell concentration treatment system A' as illustrated in FIG. 2, first, it is sufficient that a priming liquid bag is connected to the priming liquid bag connection portion 26, the clamps 21 and 25 are opened, and the priming liquid is stored in the storage container 3. It is sufficient that the diluent bag is attached to the diluent bag connection portion 2 thereafter.

The concentration step in the step b) is continued. Then, the concentration is sufficiently accelerated and the air bubble sensor 9a provided on the circuit 32 detects the volume of the cell concentrate in the storage container 3. Based on the detection, the pumps 13 and 14 are stopped to terminate the concentration step (c).

Thereafter, the cell suspension may be further added to the storage container 3 or the dilution step with the diluent may be performed as described above. In this case, it is sufficient that the step b) and the step c) are performed again.

Then, the collection step in the step d) is performed in the same manner as the case using the cell concentration treatment system A as illustrated in FIG. 1

As described above, usage of the cell suspension treatment system enables the cell concentrate to be produced with high accuracy, reduced loss of the cells, a reduced concern over contamination, and reduced damage on the cells.

Examples of the cells on which the concentration treatment can be performed in the invention include body stem cells having multipotency, such as induced pluripotent stem cells (iPS cells), embryonic stem cells (ES cells), mesenchymal stem cells, fat-derived mesenchymal stem cells, fat-derived stromal stem cells, multipotent adult stem cells, bone marrow stroma cells, and hematopoietic stem cells, lymphoid cells such as T cells, B cells, killer T-cells (cytotoxic T-cells), NK cells, NKT cells, and regulatory T-cells, somatic cells such as neuronal cells, myocytes, fibroblasts, hepatocytes, and cardiomyocytes including macrophages, monocytes, dendritic cells, granulocytes, erythrocytes, platelets, and the like, and cells on which treatment such as introduction, differentiation, or the like of genes has been performed. Among them, immune cells such as the granulocytes, the T cells, the B cells, the killer T-cells (cytotoxic T-cells), the NK cells, the NKT cells, the regulatory T-cells, the macrophages, and the dendritic cells can be preferably used. Further, cells related to various diseases, such as cancer cells and leukemia cells, can also be exemplified.

Further, the cell suspension that is used in the invention is not particularly limited as long as the suspension contains the above-mentioned cells. Examples thereof include a suspension obtained by performing enzyme treatment, crushing treatment, extraction treatment, decomposing treatment, supersonic treatment, or the like on living body tissues such as fat, skin, blood vessel, cornea, oral cavity, kidney, liver, pancreas, heart, nerve, muscle, prostate gland, intestine, amnion, placenta, and umbilical cord, and a cell suspension prepared by performing pretreatment such as density gradient centrifugation treatment, filtration treatment, enzyme treatment, decomposing treatment, supersonic treatment, or the like on blood or bone marrow aspirate. Moreover, a cell suspension after the above-mentioned cell is cultured using a culture solution, for example, DMEM, α-MEM, MEM, IMEM, or RPMI-1640, or a stimulating factor such as cytokine, antibody, and peptide in vitro.

EXAMPLES

Hereinafter, the invention will be described using examples.

Example 1

The concentration treatment on the cell suspension was performed using the cell suspension treatment system A as illustrated in FIG. 1.

All of the clamps 21, 22, 23, and 24 were in a closed state.

A cell suspension obtained by culturing jurkat cells in an RPMI-1640 culture medium containing 10% FBS was used.

The bag storing therein the cell suspension was connected to the cell culture bag connection portion 1 and the bag storing therein the physiological saline was connected to the diluent bag connection portion 2. It was checked that the clamp 21 was opened and the clamp 22 was closed. The flow rate of the pump 12 was set to 300 mL/min and the pump 12 was driven for 60 seconds so as to cause the physiological saline to be stored in the storage container 3.

Subsequently, it was checked that the clamp 23 was opened and the clamp 24 was closed. The flow rate of the pump 13 was set to 450 mL/min and the flow rate of the pump 14 was set to 150 mL/min and the pump 13 and the pump 14 were driven. The priming in the circulation circuit 30 and the cell suspension treatment device 6 was performed. At this time, the driving direction of the pump 13 was set to the direction in which the priming liquid flows downward from the upper side in the cell suspension treatment device 6. When the air bubble sensor 11 detected air bubbles, the pump 13 and the pump 14 were stopped.

It should be noted that in order not to cause the air bubbles to enter the cell suspension treatment device 6, the pump 13 was driven in the backward direction and the liquid level of the physiological saline was returned to the vicinity of the circulation inlet port 17 on the lower portion of the storage container 3.

Then, the clamp 22 was opened and the clamp 21 was closed. The flow rate of the pump 12 was set to the 300 mL/min and the pump 12 was driven for 60 seconds so as to cause the cell suspension to be stored in the storage container 3 from the cell culture bag connection portion 1 (step (a)).

Subsequently, the flow rates of the pump 12, the pump 13, and the pump 14 were set to 200 mL/min, 450 mL/min, and 200 mL/min, respectively. The cell suspension was concentrated while being circulated in the circulation circuit 30. The feeding direction in the circulation circuit 30 was a direction in which the cell suspension flows to the cell suspension introduction port 18 of the cell suspension treatment device 6 from the circulation inlet port 17 of the storage container 3 (step (b)).

After the air bubble sensor 10 detected air bubbles, the pump 12 was stopped. Subsequently, the pump 13 and the pump 14 were driven so as to concentrate the cell suspension in the storage container 3. After the air bubble sensor 11 detected air bubbles, the pump 13 and the pump 14 were stopped (step (c)).

It should be noted that in order not to cause air bubbles to enter the cell suspension treatment device 6, the pump 13 was driven in the backward direction and the liquid level of the cell suspension was returned to the vicinity of the circulation inlet port 17 on the lower portion of the storage container 3.

Then, the clamp 21 was opened and the clamp 22 was closed. The pump 12 and the pump 13 were driven at the flow rate of 200 mL/min and 450 mL/min, respectively, for 120 seconds. The physiological saline was added into the storage container 3 and the cell suspension was diluted in the storage container 3. Subsequently, the flow rates of the pump 13 and the pump 14 were set to 450 mL/min and 200 mL/min, respectively, and the filtration and the concentration of the cell suspension were performed again. It should be noted that after the air bubble sensor 11 detected air bubbles, the pump 13 and the pump 14 were stopped.

Finally, the clamp 24 was opened and the clamp 23 was closed. The pump 13 was driven at a flow rate of 100 mL/min for 60 seconds such that the cell suspension flows in the direction to the cell suspension introduction port 18 of the cell suspension treatment device 6 from the circulation inlet port 17 of the storage container 3. Then, the cell suspension in the storage container 3, the cell suspension treatment device 6, and the circulation circuit 30 was collected to the collection container 5 through the collection path 31 (step (d)).

The collected cell suspension was the cell concentrate produced by reducing unnecessary components in the cell suspension to a target concentration. The concentration with reduced loss of cells could be performed with high accuracy because no air entered the cell suspension treatment device 6 in the priming, the concentration (b), and the concentration termination (c) steps.

A cell survival ratio calculated by dividing a cell survival rate after treatment by a cell survival rate before treatment was 99% or more and damage on the cells was not observed. It should be noted that the cell survival ratio was measured by a well-known method.

Comparative Examples 1 and 2

Figure 4:
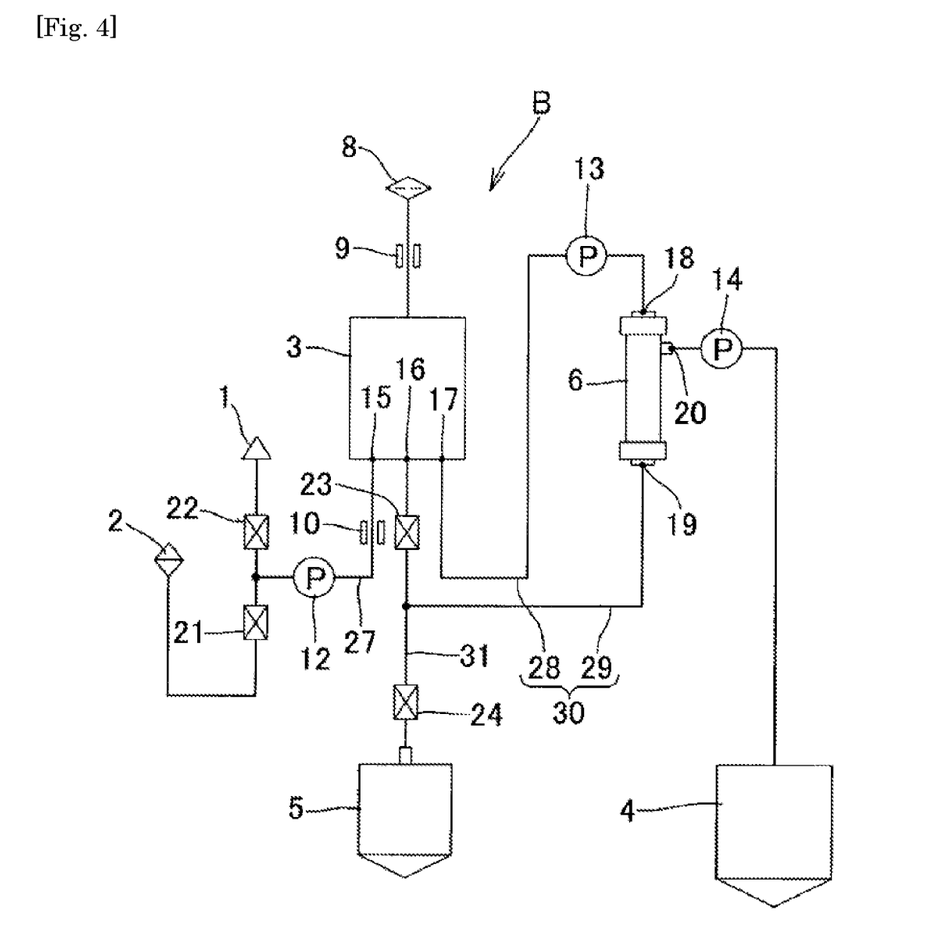
FIG. 4 is a descriptive view illustrating a cell suspension treatment system B used in comparative examples.

Treatment on the cell suspension, which was executed using a cell suspension treatment system B schematically illustrated in FIG. 4, will be described. The cell suspension treatment system B as illustrated in FIG. 4 has the same configuration as that of the cell suspension treatment system A as illustrated in FIG. 1 other than a point that the air bubble sensor 11 is not installed on the introduction communication tube 28 of the circulation circuit 30.

Further, in the comparative example 1 and the comparative example 2, the cell suspension produced under the same conditions as those in the example 1 was used but different cell culture bags were used.

A bag storing therein the cell suspension was connected to the cell culture bag connection portion 1 and a bag storing therein the physiological saline was connected to the diluent bag connection portion 2. The clamp 21 was opened and the clamp 22 was closed. The flow rate of the pump 12 was set to 300 mL/min and the pump 12 was driven for 60 seconds so as to cause the physiological saline to be stored in the storage container 3.

Subsequently, it was checked that the clamp 23 was opened and the clamp 24 was closed. The flow rate of the pump 13 was set to 450 mL/min and the flow rate of the pump 14 was set to 150 mL/min. The priming in the circulation circuit 30 and the cell suspension treatment device 6 was performed. At this time, the driving direction of the pump 13 was set to the direction in which the priming liquid flows downward from the upper side in the cell suspension treatment device 6. After the pumps 13 and 14 were driven for 100 seconds, the pumps 13 and 14 were stopped.

Then, the clamp 22 was opened and the clamp 21 was closed. The flow rate of the pump 12 was set to the 300 mL/min and the pump 12 was driven for 60 seconds so as to cause the cell suspension to be stored in the storage container 3 from the cell culture bag connection portion 1 (step (a)).

Subsequently, the pump 12, the pump 13, and the pump 14 were driven at the flow rate of 200 mL/min, 450 mL/min, and 200 mL/min, respectively. The cell suspension was concentrated while being circulated through the circulation circuit 30 between the storage container 3 and the cell suspension treatment device 6. The feeding direction in the circulation circuit 30 is a direction in which the cell suspension flows to the cell suspension introduction port 18 of the cell suspension treatment device 6 from the circulation inlet port 17 of the storage container 3 (step (b)).

After the air bubble sensor 10 detected air bubbles, the pump 12 was stopped. Subsequently, the pump 13 and the pump 14 were driven so as to concentrate the cell suspension in the storage container 3. After the pump 14 was driven for 70 seconds, the pump 13 and the pump 14 were stopped (step (c)). The driving time of the pump 14, which was 70 seconds, was time during which desired concentration can be expected to be performed in consideration of the flow rates of the pumps 12, 13, and 14.

Then, the clamp 21 was opened and the clamp 22 was closed. The flow rate of the pump 12 was adjusted to 200 mL/min and the flow rate of the pump 13 was adjusted to 450 mL/min and the pump 12 and the pump 13 were driven for 120 seconds. The physiological saline was added to the storage container 3 so as to dilute the cell suspension in the storage container 3. Subsequently, the flow rate of the pump 13 was set to 450 mL/min and the flow rate of the pump 14 was set to 200 mL/min, and the cell suspension was filtrated. After the pump 12 was driven for 120 seconds, it was stopped.

Finally, the clamp 24 was opened and the clamp 23 was closed. The pump 13 was driven at a flow rate of 100 mL/min for 60 seconds in the direction in which the cell suspension flows to the cell suspension introduction port 18 of the cell suspension treatment device 6 from the circulation inlet port 17 of the storage container 3. Then, the cell suspension in the cell suspension treatment device 6 and the circulation circuit 30 was collected to the collection container 5 through the collection path 31 (step (d)).

As a result, in the comparative example 1, in the concentration step in the step b), a volume obtained by filtration by the pump 14 within the treatment time was higher than that at the set flow rate when the pump 13 and the pump 14 were stopped although the cause was unknown. For this reason, the circulation circuit 30 was made into a state where it was not filled with the liquid sufficiently, and the cells in the collected cell suspension were lost.

Further, in the comparative example 2 executed by the same treatment method, the volume obtained by filtration by the pump 14 was smaller unlike the comparative example 1. For this reason, the volume in the storage container 3 before proceeding to the dilution step with the physiological saline was large, and an amount of the unnecessary components in the cell concentrate could not be reduced to the target concentration.

REFERENCE SIGNS LIST

1 Cell culture bag connection portion
2 Diluent bag connection portion
3 Storage container
4 Waste liquid container
5 Collection container
6 Cell suspension treatment device
7 Chamber
8 Air filter
9 Air bubble sensor
10 Air bubble sensor
11 Air bubble sensor
12 to 14 Pump
15 Solution inlet port
16 Circulation outlet port
17 Circulation inlet port
18 Cell suspension introduction port
19 Cell suspension lead-out port
20 Filtrate outlet
21 to 25, 34, 36 Clamp
26 Priming liquid bag connection portion
27 Injection path
28 Introduction communication tube
29 Lead-out communication tube
30 Circulation circuit
31 Collection path
32 Circuit
33 Collection port
35 Cell concentrate collection port
A, A', A" Cell suspension treatment system
B Cell suspension treatment system used in comparative examples 1 and 2

The invention claimed is:

1. A cell suspension treatment system comprising:
   a storage container of a cell suspension, which has a solution inlet port, a circulation outlet port, and a circulation inlet port;
   a cell suspension treatment device for concentrating the cell suspension by separating liquid from the cell suspension by filtration, the device including a container having a cell suspension introduction port, a cell suspension lead-out port, and a filtrate outlet, which is filled with a hollow fiber separation membrane,
   a circulation circuit for concentrating the cell suspension while circulating the cell suspension between the storage container and the cell suspension treatment device, the circuit being constituted by an introduction communication tube communicating the circulation inlet port of the storage container and the cell suspension introduction port of the cell suspension treatment device and a lead-out communication tube communicating the cell suspension lead-out port of the cell suspension treatment device and the circulation outlet port of the storage container;
   a collection container for collecting a cell concentrate obtained by concentration;
   a collection path for feeding the cell concentrate in the storage container, the cell suspension treatment device, and the circulation circuit to the collection container;
   an injection path for injecting a solution into the solution inlet port of the storage container;
   a detecting unit for detecting a volume of the cell concentrate in the storage container or the introduction communication tube of the circulation circuit;
   an air bubble sensor on a path from the storage container to an air filter, wherein the air filter is provided above the storage container so as to make a pressure of an inner portion of the storage container to an atmospheric pressure; and
   a controller that controls the detecting unit to detect concentration of the cell concentrate to a predetermined volume and terminates feeding of the cell concentrate to the cell suspension treatment device from the storage container.

2. The cell suspension treatment system according to claim 1, wherein the detecting unit for detecting the volume in the circulation circuit is an air bubble sensor provided on the introduction communication tube of the circulation circuit.

3. The cell suspension treatment system according to claim 1, wherein the detecting unit for detecting the volume in the storage container is an air bubble sensor provided on a circuit parallel with the storage container and communicating with a lower portion of the storage container.

4. The cell suspension treatment system according to claim 3, wherein a chamber is provided on the circuit communicating with the lower portion of the storage container.

5. The cell suspension treatment system according to claim 1, wherein an air bubble sensor is provided on the injection path.

6. The cell suspension treatment system according to claim 1, wherein all the solution inlet port, the circulation outlet port, and the circulation inlet port are provided on a lower portion of the storage container.

7. The cell suspension treatment system according to claim 1, wherein a ventilation hole is provided in the vicinity of an upper portion of the storage container and an inner portion of the storage container is an atmospheric opening system.

* * * * *